(12) United States Patent
Ghione et al.

(10) Patent No.: US 10,245,141 B2
(45) Date of Patent: Apr. 2, 2019

(54) IMPLANT DEVICE AND IMPLANTATION KIT

(71) Applicant: Sorin Group Italia S.r.l., Milan (IT)

(72) Inventors: Laura Ghione, Turin (IT); Paolo Gaschino, Turin (IT); Monica Francesca Achiluzzi, Chivasso (IT)

(73) Assignee: Sorin Group Italia S.r.l., Milan (IT)

( * ) Notice: Subject to any disclaimer, the term of this patent is extended or adjusted under 35 U.S.C. 154(b) by 180 days.

(21) Appl. No.: 15/310,701

(22) PCT Filed: May 14, 2014

(86) PCT No.: PCT/IB2014/061436
§ 371 (c)(1),
(2) Date: Nov. 11, 2016

(87) PCT Pub. No.: WO2015/173609
PCT Pub. Date: Nov. 19, 2015

(65) Prior Publication Data
US 2017/0071733 A1    Mar. 16, 2017

(51) Int. Cl.
*A61F 2/24*    (2006.01)

(52) U.S. Cl.
CPC .............. *A61F 2/24* (2013.01); *A61F 2/2412* (2013.01); *A61F 2/2418* (2013.01);
(Continued)

(58) Field of Classification Search
CPC ........ A61F 2/24; A61F 2/2436; A61F 2/2418; A61F 2/2412; A61F 2/2433;
(Continued)

(56) References Cited

U.S. PATENT DOCUMENTS

| 5,855,601 A | 1/1999 | Bessler et al. |
| 6,287,339 B1 | 9/2001 | Vazquez et al. |

(Continued)

FOREIGN PATENT DOCUMENTS

| CN | 102869319 A | 1/2013 |
| EP | 0133420 B1 | 2/1988 |

(Continued)

OTHER PUBLICATIONS

International Preliminary Report on Patentability issued in PCT/IB2014/061436, dated Nov. 24, 2016, 7 pages.
(Continued)

*Primary Examiner* — Julian W Woo
(74) *Attorney, Agent, or Firm* — Faegre Baker Daniels LLP

(57) ABSTRACT

An implant device (V), such as a heart valve, for implantation in an animal body includes an annular structure and one or more elongated anchoring members deployable to a deployed condition for insertion into an animal body. The anchoring members are retractable from the deployed condition to a rolled up condition wherein the anchoring members protrude radially out from the annular structure of the device (V) to provide anchoring to a body structure (AS) of an animal. In the rolled up condition the anchoring members at least partly protrude axially of the annular structure of the device (V).

20 Claims, 10 Drawing Sheets

(52) U.S. Cl.
CPC .......... *A61F 2/2433* (2013.01); *A61F 2/2436* (2013.01); *A61F 2/2409* (2013.01); *A61F 2/2427* (2013.01); *A61F 2/2439* (2013.01); *A61F 2210/0014* (2013.01)

(58) Field of Classification Search
CPC .................. A61F 2/2427; A61F 2/2409; A61F 2210/0014; A61F 2/2439
See application file for complete search history.

(56) References Cited

U.S. PATENT DOCUMENTS

| | | |
|---|---|---|
| 6,312,465 B1 | 11/2001 | Griffin et al. |
| 6,425,916 B1 | 7/2002 | Garrison et al. |
| 6,458,153 B1 | 10/2002 | Bailey et al. |
| 6,461,366 B1 | 10/2002 | Seguin |
| 6,530,952 B2 | 3/2003 | Vesely |
| 6,569,196 B1 | 5/2003 | Vesely |
| 6,629,534 B1 | 10/2003 | St. Goar et al. |
| 6,821,297 B2 | 11/2004 | Snyders |
| 6,974,476 B2 | 12/2005 | McGuckin, Jr. et al. |
| 7,011,661 B2 | 3/2006 | Vesely |
| 7,018,406 B2 | 3/2006 | Seguin et al. |
| 7,018,408 B2 | 3/2006 | Bailey et al. |
| 7,201,772 B2* | 4/2007 | Schwammenthal .. A61F 2/2418 623/1.24 |
| 7,252,682 B2 | 8/2007 | Seguin |
| 7,329,278 B2 | 2/2008 | Seguin et al. |
| 7,381,220 B2 | 6/2008 | Macoviak et al. |
| 7,556,646 B2 | 7/2009 | Yang et al. |
| 7,585,321 B2 | 9/2009 | Cribier |
| 7,648,528 B2 | 1/2010 | Styrc |
| 7,708,775 B2 | 5/2010 | Rowe et al. |
| 7,717,955 B2 | 5/2010 | Lane et al. |
| 7,753,949 B2 | 7/2010 | Lamphere et al. |
| 7,758,640 B2 | 7/2010 | Vesely |
| 7,776,083 B2 | 8/2010 | Vesely |
| 7,806,927 B2 | 10/2010 | Styrc |
| 7,892,281 B2 | 2/2011 | Seguin et al. |
| 7,959,672 B2 | 6/2011 | Salahieh et al. |
| 8,016,882 B2 | 9/2011 | Macoviak et al. |
| 8,025,695 B2 | 9/2011 | Fogarty et al. |
| 8,048,153 B2 | 11/2011 | Salahieh et al. |
| 8,070,802 B2 | 12/2011 | Lamphere et al. |
| 8,105,375 B2 | 1/2012 | Navia et al. |
| 8,167,935 B2 | 5/2012 | McGuckin, Jr. et al. |
| 8,221,493 B2 | 7/2012 | Boyle et al. |
| 8,236,049 B2 | 8/2012 | Rowe et al. |
| 8,287,591 B2 | 10/2012 | Keidar et al. |
| 8,323,335 B2 | 12/2012 | Rowe et al. |
| 8,398,708 B2 | 3/2013 | Meiri et al. |
| 8,403,983 B2 | 3/2013 | Quadri et al. |
| 8,414,644 B2 | 4/2013 | Quadri et al. |
| 8,449,599 B2 | 5/2013 | Chau et al. |
| 8,454,686 B2 | 6/2013 | Alkhatib |
| 8,540,767 B2 | 9/2013 | Zhang |
| 8,579,964 B2 | 11/2013 | Lane et al. |
| 8,579,966 B2 | 11/2013 | Seguin et al. |
| 8,597,348 B2 | 12/2013 | Rowe et al. |
| 9,186,249 B2 | 11/2015 | Rolando et al. |
| 9,532,870 B2* | 1/2017 | Cooper ................. A61F 2/2418 |
| 10,034,750 B2* | 7/2018 | Morriss ................ A61F 2/2418 |
| 2005/0137691 A1 | 6/2005 | Salahieh et al. |
| 2005/0182486 A1 | 8/2005 | Gabbay |
| 2006/0195183 A1 | 8/2006 | Navia et al. |
| 2007/0043435 A1 | 2/2007 | Seguin et al. |
| 2008/0140189 A1 | 6/2008 | Nguyen et al. |
| 2008/0208327 A1 | 8/2008 | Rowe |
| 2009/0125098 A1 | 5/2009 | Chuter |
| 2009/0248149 A1 | 10/2009 | Gabbay |
| 2009/0276040 A1 | 11/2009 | Rowe et al. |
| 2010/0004739 A1 | 1/2010 | Vesely |
| 2010/0145440 A1 | 6/2010 | Keranen |
| 2010/0174363 A1 | 7/2010 | Castro |
| 2010/0256741 A1 | 10/2010 | Hansen |
| 2010/0312333 A1 | 12/2010 | Navia et al. |
| 2011/0029072 A1 | 2/2011 | Gabbay |
| 2011/0071624 A1 | 3/2011 | Finch et al. |
| 2011/0098800 A1 | 4/2011 | Braido et al. |
| 2011/0137397 A1 | 6/2011 | Chau et al. |
| 2011/0166636 A1 | 7/2011 | Rowe |
| 2011/0178597 A9 | 7/2011 | Navia et al. |
| 2011/0218620 A1 | 9/2011 | Meiri et al. |
| 2011/0224785 A1 | 9/2011 | Hacohen |
| 2011/0313515 A1 | 12/2011 | Quadri et al. |
| 2011/0319989 A1* | 12/2011 | Lane .................... A61F 2/2418 623/2.11 |
| 2012/0010697 A1 | 1/2012 | Shin et al. |
| 2012/0016464 A1 | 1/2012 | Seguin |
| 2012/0022640 A1 | 1/2012 | Gross et al. |
| 2012/0046742 A1 | 2/2012 | Tuval et al. |
| 2012/0078353 A1 | 3/2012 | Quadri et al. |
| 2012/0078360 A1 | 3/2012 | Rafiee |
| 2012/0101571 A1 | 4/2012 | Thambar et al. |
| 2012/0165930 A1 | 6/2012 | Gifford, III et al. |
| 2012/0303116 A1 | 11/2012 | Gorman et al. |
| 2013/0018449 A1 | 1/2013 | Bailey et al. |
| 2013/0035759 A1 | 2/2013 | Gross et al. |
| 2013/0053950 A1 | 2/2013 | Rowe et al. |
| 2013/0144381 A1 | 6/2013 | Quadri et al. |
| 2013/0211508 A1 | 8/2013 | Lane et al. |
| 2013/0245753 A1 | 9/2013 | Alkhatib |
| 2013/0253643 A1 | 9/2013 | Rolando et al. |
| 2014/0046434 A1 | 2/2014 | Rolando et al. |
| 2016/0193044 A1 | 7/2016 | Achiluzzi |

FOREIGN PATENT DOCUMENTS

| | | |
|---|---|---|
| EP | 0155245 B1 | 5/1990 |
| EP | 0515324 B1 | 11/1992 |
| EP | 1233731 B1 | 11/1999 |
| EP | 1049425 B1 | 11/2000 |
| EP | 1176913 B1 | 2/2002 |
| EP | 1251803 B1 | 10/2002 |
| EP | 1335683 B1 | 8/2003 |
| EP | 1343438 B1 | 9/2003 |
| EP | 1401359 B1 | 3/2004 |
| EP | 1408850 B1 | 4/2004 |
| EP | 1562502 A1 | 8/2005 |
| EP | 1562522 B1 | 8/2005 |
| EP | 1621162 B1 | 2/2006 |
| EP | 1701668 B1 | 9/2006 |
| EP | 1758523 B1 | 3/2007 |
| EP | 1935378 A1 | 6/2008 |
| EP | 1690515 B1 | 7/2008 |
| EP | 2000115 B1 | 12/2008 |
| EP | 2072027 A1 | 6/2009 |
| EP | 2078498 B1 | 7/2009 |
| EP | 2138132 B1 | 12/2009 |
| EP | 2250976 A1 | 11/2010 |
| EP | 2258312 B1 | 12/2010 |
| EP | 2260796 B1 | 12/2010 |
| EP | 2260797 B1 | 12/2010 |
| EP | 2260798 B1 | 12/2010 |
| EP | 2340075 B1 | 7/2011 |
| EP | 2641569 A1 | 3/2012 |
| EP | 2476394 B1 | 7/2012 |
| EP | 2486893 A1 | 8/2012 |
| EP | 2526895 B1 | 11/2012 |
| EP | 2526898 B1 | 11/2012 |
| EP | 2526899 B1 | 11/2012 |
| EP | 2529696 B1 | 12/2012 |
| EP | 2529697 B1 | 12/2012 |
| EP | 2529698 B1 | 12/2012 |
| EP | 2529699 B1 | 12/2012 |
| EP | 2537487 B1 | 12/2012 |
| EP | 2695586 A1 | 2/2014 |
| EP | 2886083 A1 | 6/2015 |
| WO | WO2008091515 A2 | 7/2008 |
| WO | WO2011044994 A1 | 4/2011 |
| WO | WO2012063228 A1 | 5/2012 |
| WO | WO2013037805 A1 | 3/2013 |
| WO | WO2013075215 A1 | 5/2013 |

(56) References Cited

FOREIGN PATENT DOCUMENTS

| WO | WO2013082454 A1 | 6/2013 |
| WO | WO2013096541 A1 | 6/2013 |
| WO | 2013128436 A1 | 9/2013 |

OTHER PUBLICATIONS

International Preliminary Report on Patentability issued in PCT/IB2014/063176, dated Feb. 18, 2016, 9 pages.
European Search Report issued in EP Application No. 12425060, completed Jun. 27, 2012, 7 pages.
European Search Report issued in EP Application No. 12425139, completed Jan. 16, 2013, 7 pages.
European Search Report issued in EP Application No. 13425113, dated Feb. 7, 2014, 6 pages.
International Search Report issued in PCT/IB2013/052090, dated Jul. 21, 2013, 4 pages.
International Search Report issued in PCT/IB2014/063176, dated Oct. 9, 2014, 12 pages.
International Search Report and Written Opinion issued in PCT/IB2014061436, dated Oct. 20, 2014, 9 pages.

\* cited by examiner

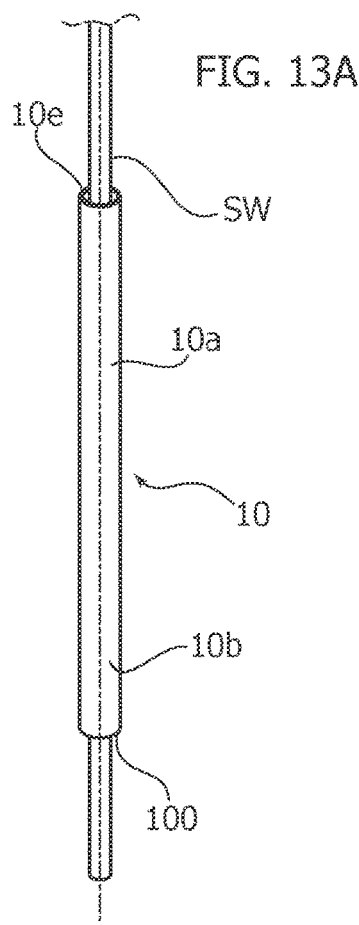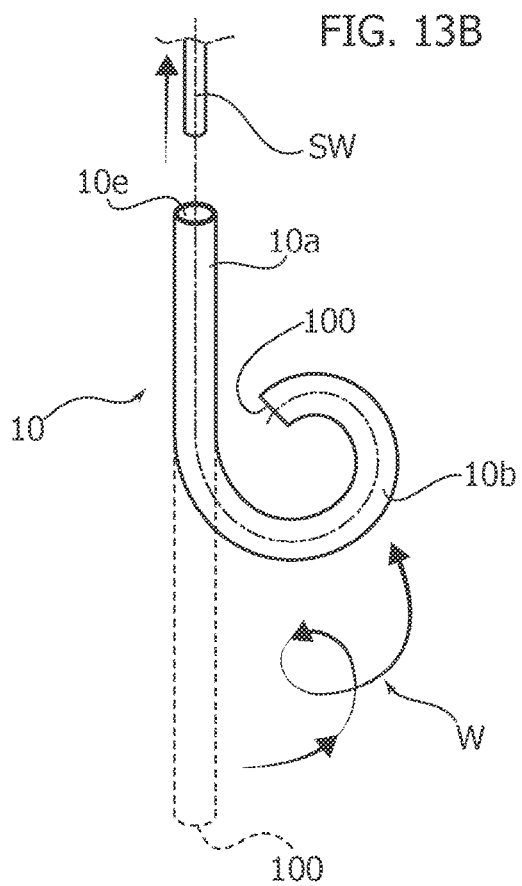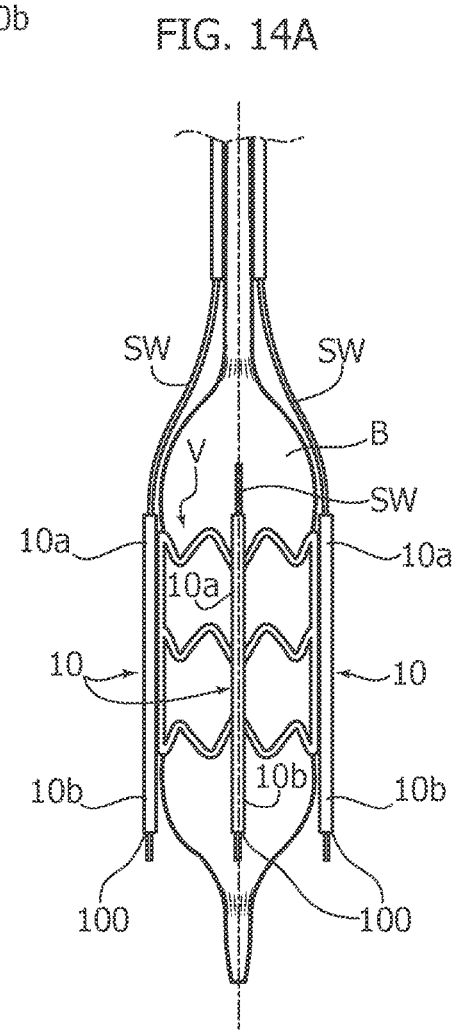

FIG. 16B
FIG. 16C
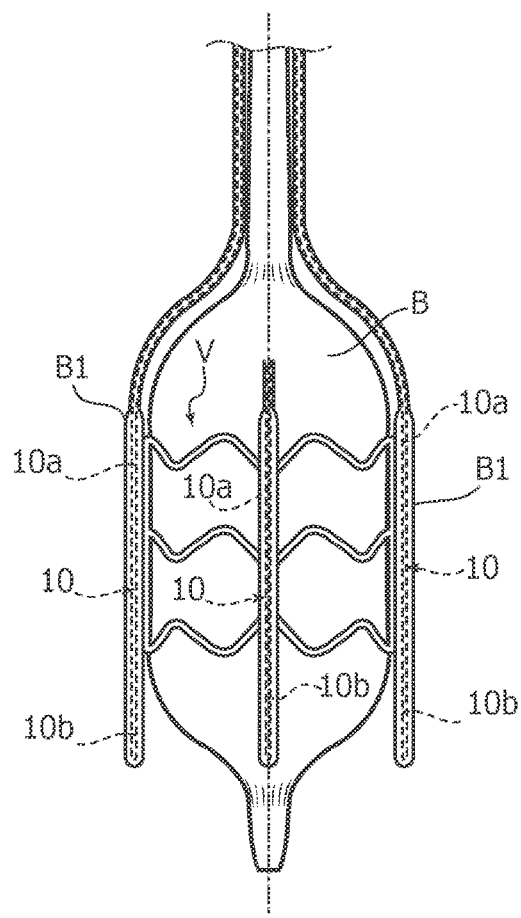
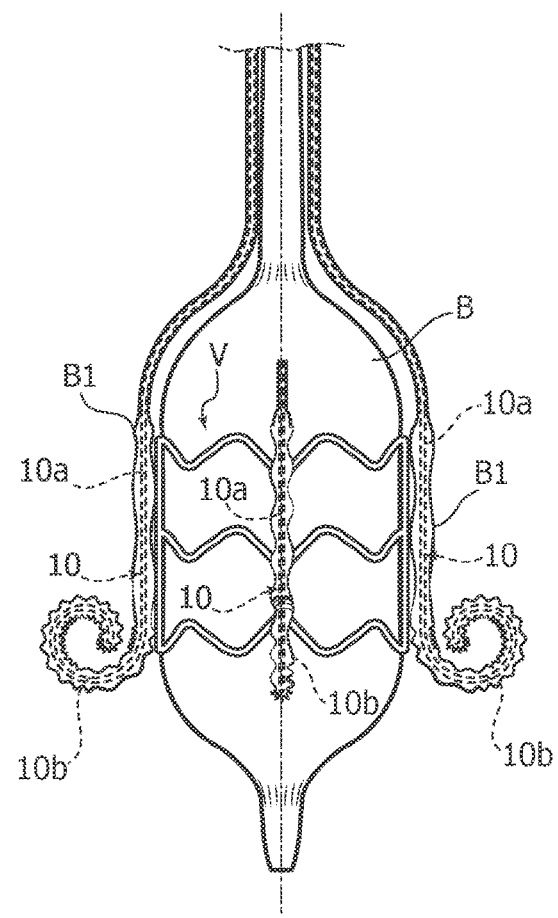

IMPLANT DEVICE AND IMPLANTATION KIT

CROSS-REFERENCE TO RELATED APPLICATION

This application is a national stage application of PCT/IB2014/061436, internationally filed May 14, 2014, which is herein incorporated by reference in its entirety.

TECHNICAL FIELD

This description relates to implant devices.

One or more embodiments may relate to implant devices such as prosthetic heart valves.

One or more embodiments may be used for sutureless implantation of implant devices by a minimally invasive approach.

BACKGROUND

Implant devices may be used to treat various pathologies by being implanted in the body of an animal such as a human. Implantation of such devices may require that the implant device is anchored to a structure of the body such as e.g. a cardiac site such as a valvular site or annulus.

A variety of anchoring members have been devised for anchoring implant devices to a structure in an animal body.

For instance, cardiac rhythm management devices such as e.g. pacemakers, defibrillators, cardioverters and electrodes possibly associated therewith may be provided with anchoring members including barbs. Self-anchoring electrodes such as so-called pigtail electrodes may be used in such a context.

Barbs may also be used as anchoring members for valve prostheses, while anchoring members adapted to extend into the sinuses of Valsalva may be used for anchoring valve prostheses at an aortic annulus site.

EP 2 695 586 A1 describes anchoring members including a web portion coupled to the annular structure of a valve prosthesis and two end portions at axially opposed sides of the web portion. The end portions admit (that is, are adapted to assume e.g. by moving to and/or being brought to) an insertion condition where the end portions are aligned to the web portion and extend axially with respect to the annular structure and an anchoring condition where the end portions extend at an angle to the web portion radially outwardly of the annular structure to provide anchoring of the prostheses proximally and distally, respectively, of an annulus.

In certain implementations of apparatus for replacing a diseased cardiac valve as disclosed in US 2010/0312333 A1, first and second attachment members can also comprise windable coils located at the first and second ends of an elongated body member to respectively contact the superior and inferior aspects of a native mitral annulus when the apparatus is in an expanded configuration.

SUMMARY

One or more embodiments may provide implant devices adapted to be anchored to a structure in an animal body by allowing sutureless implantation by a minimally invasive approach.

One or more embodiments may provide one or more anchoring members adapted for use with collapsible devices, e.g. prostheses.

One or more embodiments may permit implantation by minimally affecting the implantation site e.g. by avoiding expansion or dilation of an implantation site.

One or more embodiments may permit anchoring an implant device at implantation sites which are intrinsically soft and/or damaged by ensuring firm anchoring of the implant device.

One or more embodiments may permit implantation of an implant device where the anchoring member(s) grasp(s) a body structure with minimal stresses applied onto such structure.

One or more embodiments are adapted for association with a variety of implant devices.

One or more embodiments may permit implantation by avoiding, or at least minimizing, the amount a cardiac replacement valve may protrude into a heart chamber e.g. the amount a mitral replacement valve may protrude into a ventricular chamber.

One or more embodiments may be delivered and deployed at an implantation site by means of a structurally simple, little obtrusive delivery tool including e.g. one or more of the following: a sheath, a wire-like mandrel or an inflatable catheter balloon.

One or more embodiments may thus include, among other features:

Embodiment 1

An implant device for implantation in an animal body, the device including an annular structure extending axially between opposed ends and at least one elongated anchoring member deployable to a deployed condition for insertion into an animal body and retractable from said deployed condition to a rolled up condition wherein the anchoring member protrudes radially outwardly of the annular structure of the device to provide anchoring of the implant device to a body structure of an animal, wherein in said rolled up condition the anchoring member at least partly protrudes axially outwardly of the annular structure of the device.

Embodiment 2

The implant device of Embodiment 1, wherein the at least one elongated anchoring member includes a proximal portion which retains the deployed condition and a distal portion subject to winding from the deployed condition to the rolled up condition.

Embodiment 3

The implant device of Embodiment 1 or Embodiment 2, wherein the anchoring member is located at one end of the annular structure of the device and includes a distal portion, which, in said rolled up condition, extends in a trajectory centered around a point coplanar with said one end of the annular structure of the device.

Embodiment 4

The implant device of any of the previous Embodiments, wherein the anchoring member includes a proximal portion coextensive with the annular structure of the device and a distal portion extending away from the annular structure of the device, wherein in said rolled up condition, the region of the said distal portion adjacent to said proximal portion has an axial orientation with respect to the annular structure of the device.

Embodiment 5

The implant device of any of the previous Embodiments, wherein the at least one elongated anchoring member includes elastic material, whereby the anchoring member is deployable to the deployed condition and elastically returns to the rolled up condition from the deployed condition.

Embodiment 6

The implant device of any of the previous Embodiments, wherein the at least one elongated anchoring member includes shape memory material, whereby the anchoring member returns to the rolled up condition from the deployed condition by shape memory effect, preferably due to energy applied to the shape memory material.

Embodiment 7

The implant device of any of the previous Embodiments, wherein the at least one elongated anchoring member includes material selected out of one or combinations of flexibly resilient materials, medical grade materials, metal materials, plastics materials, shape memory materials, preferably out of Nitinol and stainless steel.

Embodiment 8

The implant device of any of the previous Embodiments, wherein winding of the at least one elongated anchoring member from the deployed condition to the rolled up condition is with a winding trajectory which is spiral-shaped or helix-shaped.

Embodiment 9

The implant device of any of the previous Embodiments, wherein winding of the at least one elongated anchoring member from the deployed condition to the rolled up condition is with a winding trajectory having an angular extent in excess of 360°.

Embodiment 10

The implant device of any of the previous Embodiments, wherein winding of the at least one elongated anchoring member from the deployed condition to the rolled up condition is with a winding trajectory having an angular extent between 180° and 900°.

Embodiment 11

The implant device of any of the previous Embodiments, wherein the at least one elongated member is blade-like or wire-like.

Embodiment 12

The implant device of any of the previous Embodiments, wherein the at least one elongated member is of solid cross-section or tubular.

Embodiment 13

The implant device of any of the previous Embodiments, wherein the device includes a prosthetic heart valve, preferably mitral.

Embodiment 14

An implantation kit for an implant device including:
an implant device according to any of Embodiments 1 to 13,
at least one constraint member to cooperate with the at least one anchoring member to constrain the at least one anchoring member to the deployed condition during insertion into an animal body and to permit winding of the at least one anchoring member to a rolled up condition to provide anchoring of the implant device to a body structure of an animal.

Embodiment 15

The kit of Embodiment 14, wherein the at least one constraint member includes a tubular sheath extending along an axis, the tubular sheath maintaining the at least one anchoring member in the deployed condition by confining the at least one anchoring member radially of said axis, the tubular sheath withdrawable along said axis to at least partly uncover the at least one anchoring member to permit winding thereof to the rolled up condition.

Embodiment 16

The kit of Embodiment 14, wherein the at least one anchoring member is tubular with a longitudinal cavity and the at least one constraint member includes a wire member for insertion into the longitudinal cavity of the at least one anchoring member to maintain the at least one anchoring member in the deployed condition, the wire member extractable from the longitudinal cavity of the at least one anchoring member to permit winding thereof to the rolled up condition.

Embodiment 17

The kit of Embodiment 14, wherein the at least one constraint member includes an inflatable balloon element vested onto the at least one anchoring member to form a tubular tunic therearound, the inflated balloon to maintain the at least one anchoring member to the deployed condition and deflatable to permit winding of the at least one anchoring member to the rolled up condition.

BRIEF DESCRIPTION OF THE DRAWINGS

One or more embodiments will now be described, purely by way of non-limiting example, with reference to the annexed figures, wherein:

FIGS. 13A, 13B and 14A-14C are a second set of figures exemplary of implantation of embodiments, and FIGS. 15A, 15B and 16A-16C are a third set of figures exemplary of implantation of embodiments.

DETAILED DESCRIPTION

Figure 1:
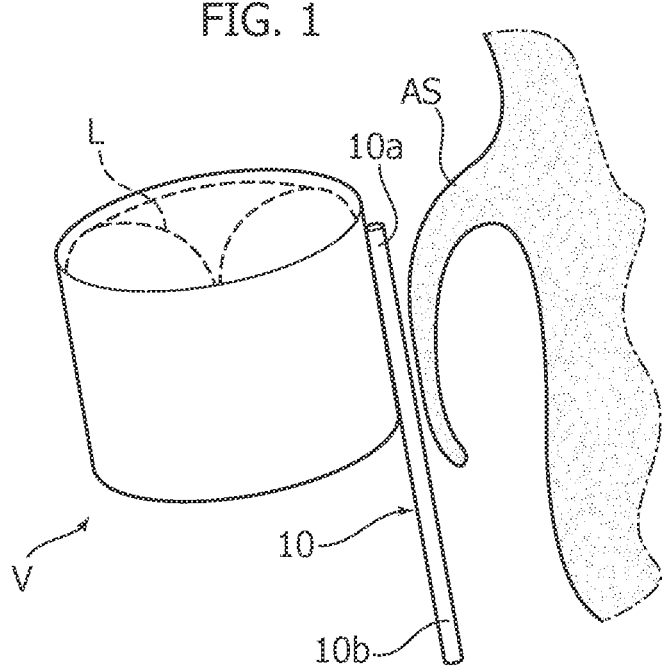
FIGS. 1 and 2 are exemplary of principles of operation of embodiments.

In the following description, numerous specific details are given to provide a thorough understanding of various exemplary embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The sizes and relative positions of elements in the figures are not necessarily drawn to scale. For example, the shapes of various elements and angles may not be drawn to scale, and some of these elements may be enlarged and positioned to improve drawing legibility. Further, the particular shapes of the elements as drawn are not intended to convey any information regarding the actual shape of the particular elements and have been solely selected for ease of recognition in the drawings.

The headings and reference signs provided herein are for the reader's convenience only and do not interpret the scope or meaning of the embodiments.

Figure 2:
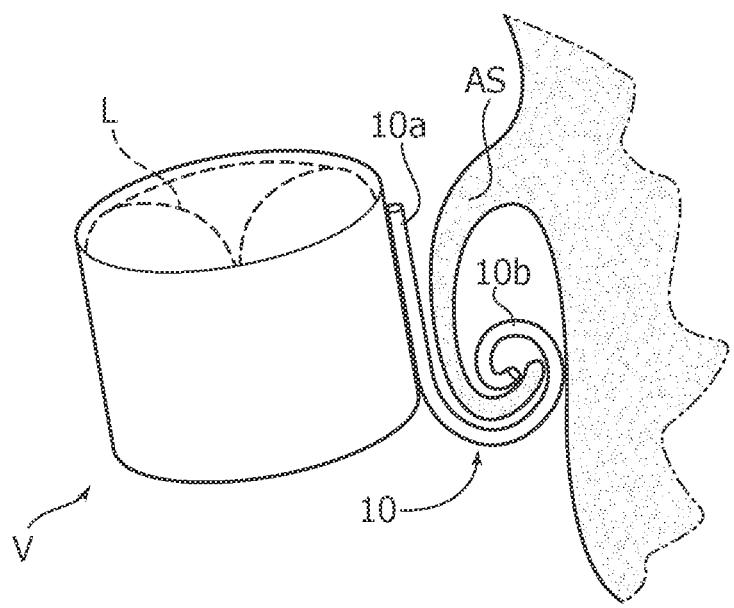

FIGS. 1 and 2 are schematically representative of implantation of an implant device V such as e.g. a valve prosthesis at an implantation site such as e.g. a heart site such as a mitral valve site.

Figure 3:
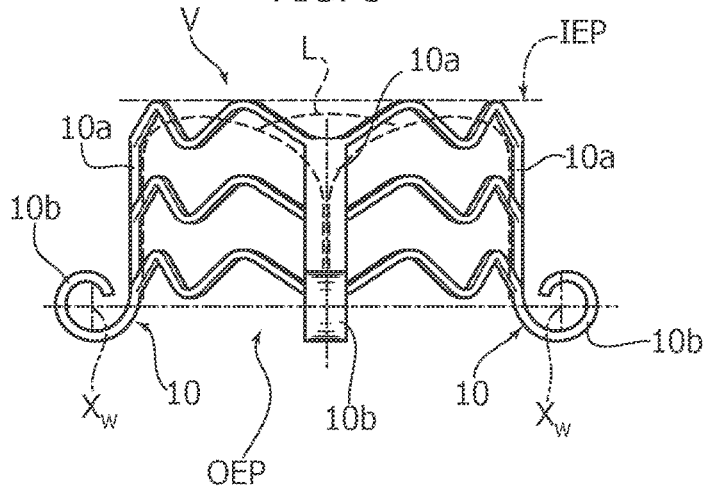
FIGS. 3 to 5 are exemplary of embodiments of implant devices.

In one or more embodiments, such a valve prosthesis V may include one or more prosthetic leaflets L as schematically shown in dashed lines in FIGS. 1 to 3.

The valve prosthesis V is schematically represented as an annular structure (body member) intended to be anchored at an annular site AS by means of one or more anchoring members 10. Only one such anchoring member is shown in FIGS. 1 and 2 for ease of illustration.

In one or more embodiments, the valve prosthesis V may be of a type adapted to be implanted by adopting a "sutureless" approach e.g. via non-invasive thoracic (micro)surgery or via percutaneous procedure.

In one or more embodiments, the valve prosthesis V may be a collapsible valve prosthesis.

The exemplary representation of FIGS. 1 and 2 refers to an implantation approach which involves the conservation of the native valve structures e.g. the leaflets (and the chordae tendinae, not visible in the schematic representation of FIGS. 1 and 2).

The representation of FIGS. 1 and 2 is schematically exemplary of the annular site AS, that is the structure(s) of the body of the patient to which the implant device V is intended to be anchored.

In various possible contexts of use, the body structure in question (e.g. the native leaflets) may be soft and/or weakened (e.g. due to a pathological state) and thus little able to support stresses.

As exemplified in FIG. 2, anchoring members 10 as per one or more embodiments are adapted to cooperate with such a body structure by "grasping" it, that is by wrapping/winding to a rolled up condition where the body structure (e.g. the native leaflets) may become firmly yet gently entrapped in the convoluted shape of the anchoring member once rolled up.

The schematic representation of a valve prosthesis of FIGS. 1 and 2 is exemplary of the applicability of one or more embodiments to devices such as e.g. different types of valve prostheses (a mitral valve prosthesis being just one possible choice among various valve types) and, more generally, to other types of implant devices such as e.g. stents (e.g. peripheral stents), stent-grafts, cardiac rhythm management devices and so on.

Also, while one anchoring member 10 is shown in FIGS. 1 and 2 located at one end of the device V for simplicity of representation, plural anchoring members 10 (identical or having different sizes/shapes and configurations) may be associated to either or both ends of a single implant device V.

Plural anchoring members 10 as illustrated in FIGS. 1 and 2 distributed with uniform/non-uniform spacing around an implant device such as a prosthetic valve may be exemplary of such arrangements including plural anchoring members.

In one or more embodiments, the anchoring members may be spaced 90 degrees apart.

In one or more embodiments, the anchoring members may be placed in opposing pairs, e.g. opposing pairs spaced 10-60 degrees apart.

Such a placement may optionally match the typical anatomy of a mitral valve.

As shown in FIGS. 1 and 2, one or more embodiments of an anchoring member 10 may include an elongated element deployable to a deployed (e.g. expanded) condition—see e.g. FIG. 1—for insertion in an animal body e.g. for locating the implant device V at an implantation site AS and retractable (collapsible) by winding/wrapping to a rolled up collapsed condition—see e.g. FIG. 2—where the anchoring member grasps, that is captures a structure of a patient's body (e.g. the annular site AS as exemplified by the natural valve leaflets illustrated in FIGS. 1 and 2) to anchor the implant device V at the implantation site.

In one or more embodiments, the anchoring member 10 may include an elastic (optionally superelastic) material and be configured to be elastically biased towards the rolled up (collapsed) condition of FIG. 2: that is, in the absence of forces applied, the anchoring member will assume the rolled up condition.

The member 10 may thus be deployed (e.g. unwound) to the extended condition of FIG. 1, maintained in such a condition (e.g. by one of the constraint members as exemplified in the following) and then permitted (e.g. by being released by the constraint member) to return e.g. (super) elastically to the rolled up condition of FIG. 2.

Exemplary of materials adapted to exhibit such a behavior are any one or combination of flexibly resilient, medical grade materials including, for example, Nitinol, stainless steel, or other suitable metal or plastics having e.g. shape memory characteristics.

In one or more embodiments, the anchoring member 10 may include a shape memory material and be configured to pass from the deployed condition of FIG. 1 to the rolled up condition of FIG. 2 via a shape memory effect, optionally stimulated by the application of e.g. thermal, optical or electrical energy.

Materials such as Nitinol may exhibit both elastic/superelastic properties and shape memory behavior and are thus cited as exemplary of both.

In one or more embodiments, the anchoring member 10 may include a proximal portion 10a which retains the deployed condition (e.g. in FIGS. 1 and 2 the portion 10a substantially maintains the same rectilinear shape) and a distal portion 10b which is subject to rolling up. In one or more embodiments, when in the rolled up condition, the anchoring member 10 may thus be generally hook-shaped.

As used herein, "proximal" and "distal" may refer to the coupling condition of the anchoring member 10 to the implant device V. The "distal" portion 10b subject to rolling up may thus be the portion of the anchoring member 10 opposed to the implant device V which is intended to cooperate with the patient body structure in anchoring the implant device at the implantation site.

Figure 4:
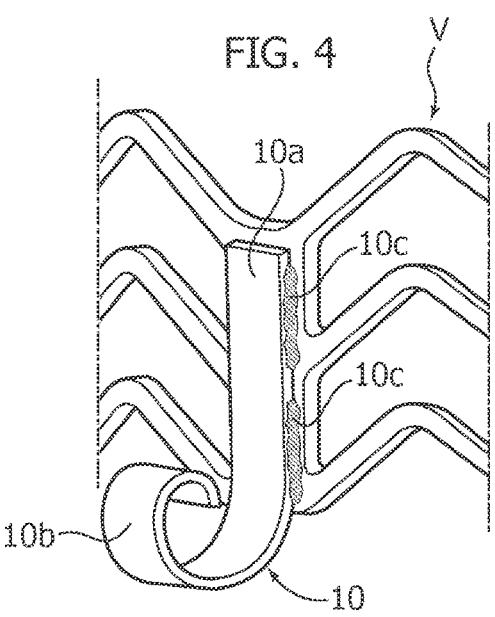
Figure 5:
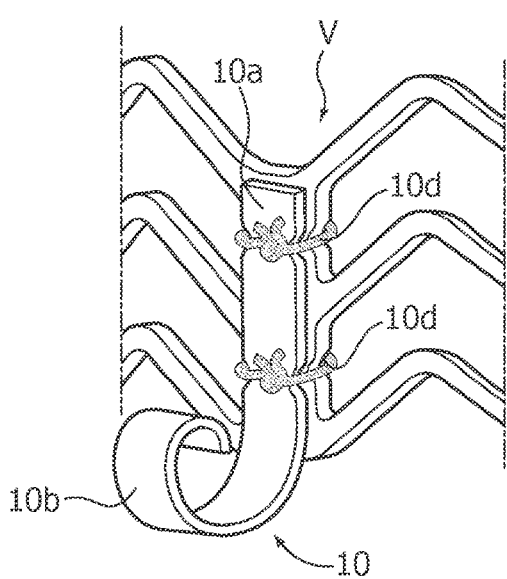

FIGS. 3 to 5 are exemplary of one or more embodiments of an implant device including one or more anchoring members 10. Throughout FIGS. 3 to 5 an implant device V is exemplified in the form of a valve prosthesis (e.g. mitral) including an annular structure or body member such as a radially expandable stent-like support armature for the valve leaflets L (not visible in certain figures).

As shown in FIGS. 3 to 5, the stent-like structure may include plural annular members having a zig-zag pattern staggered along the axial direction of the stent structure, these annular members being connected by axial connection members or "links".

FIGS. 3 to 5 are exemplary of one or more embodiments of an implant device V including an annular (e.g. tubular) stent-like body or support structure (armature) extending axially—e.g. in an axial direction of the annular structure— between opposed ends of the device V. In the (purely exemplary) case of valve prosthesis as shown herein, the device may include two end openings at least approximately lying in respective notional end planes IEP and OEP.

In exemplary embodiments for use e.g. at a mitral implantation site the end planes IEP and OEP correspond to blood inflow and blood outflow openings from the left atrium into the left ventricle of the heart.

A desirable feature in such possible implantation is that the amount the implant device V protrudes into the ventricular chamber is reduced in order to minimize possible interference with (natural or prosthetic) aortic valve operation to control blood flow from the left ventricle into the aorta.

FIG. 3 refers to an exemplary embodiment where four anchoring members 10 (angularly spaced 90° to one another over the valve periphery) may be one-piece with the armature of the implant device.

In one or more embodiments, the proximal portions 10a of the anchoring members 10 may also form the links of the stent structure.

As shown in FIG. 3, in one or more embodiments, the anchoring members 10 may be arranged (e.g. positioned, dimensioned and shaped) in such a way that in a rolled up (collapsed) condition wherein they provide anchoring of the implant device V to the body structure AS (see also FIG. 2 or FIG. 12C) the anchoring members 10 may at least partly protrude radially outwardly of the annular structure of the device V while also at least partly protruding axially outwardly of the annular structure of the device V. That is, in one or more embodiments, in the rolled up (collapsed) condition the anchoring members 10 may at least partly protrude with respect to the end plane OEP of the annular structure of the device V to which they are associated.

In one or more embodiments, this result may be achieved by causing (the distal portion 10b of) the anchoring members 10 to be finally rolled up—that is wound up in the collapsed implantation condition—according to a e.g. spiral or helix-like trajectory centered around a point $X_W$ which is coplanar with the end plane OEP.

Such a central region of the (final) rolled up/wound trajectory of the anchoring members 10 may be notionally identified as a center point of the trajectory. In one or more embodiments, design factors and/Or tolerances inherently associated with manufacturing the implant devices exemplified herein, may cause such a trajectory to correspond only approximately to a geometric curve having a single center point. For that reason, reference has been made previously to a trajectory centered e.g. having a locus of curvature points located "around", that is in the vicinity of a point $X_W$ which is coplanar with the end plane OEP.

In one or more embodiments, the result of having the anchoring members 10 at least partly protrude axially outwardly of the annular structure of the device V (also) in the collapsed implantation condition may be achieved by having the root of the distal portion 10b, that is the region of the distal portion 10b adjacent to the proximal portion 10a of the anchoring members 10 to retain an axial orientation with respect to the annular structure of the device, while the rest of the distal portion 10b undergoes the rolling up/winding movement towards the collapsed condition.

In one or more embodiments the device V may thus include one or more anchoring members 10 including a proximal portion 10a coextensive with the annular structure of the device V and a distal portion 10b extending away from the annular structure of the device V: in the rolled up (collapsed) condition, the region of the distal portion 10a adjacent to the proximal portion 10a (that is adjacent to the annular structure of the device) in any case retains an axial orientation with respect to the annular structure of the device V.

One or more embodiments as exemplified herein thus make it possible to minimize the amount the implant device V protrudes into the ventricular chamber. As exemplified in FIG. 12C the (blood outflow) plane OEP will end up by being located in a recessed position with respect to the surrounding body structure AS "grasped" by the anchoring members 10 which retain the device V at the implantation site.

This is in contrast e.g. with implementations as exemplified in US 2010/0312333 A1 wherein windable coils located at the opposed ends of the body member of the device can respectively contact the superior and inferior aspects of a native mitral annulus when the apparatus is in an expanded configuration. In addition to failing to exert any grasping action on the tissues of the mitral annulus, in the collapsed implantation condition, the coils of US 2010/0312333 are completely withdrawn within the body member of the device, which will cause the device to protrude significantly and undesirably into the ventricular chamber.

FIG. 4 refers to exemplary embodiments where one or more anchoring members 10 may be coupled via welding (welding spots are schematically indicated at 10c) to the structure of the implant device (e.g. to the axial links of the stent-like structure).

FIG. 5 refers to an exemplary embodiment where one or more anchoring members 10 may be coupled to the implant device V (e.g. to the axial links of stent-like structure) via stitches. In one or more embodiments the stitches 10d may include biocompatible material such as surgical thread.

FIGS. 6 to 9 exemplify various possible embodiments of anchoring members 10 illustrated in the rolled up condition. The examples shown refer to anchoring members that have a general hook-like shape in the rolled up condition including a linear proximal portion 10a and distal portion 10b subject to winding.

FIGS. 6 to 9 exemplify the possibility for one or more embodiments to include:
- a blade-like structure (FIG. 6),
- a wire-like structure, with a solid structure, that is a solid circular cross-section (FIGS. 7 and 9),
- a tubular structure, that is having a longitudinal cavity 10d extending along the length of the anchoring member 10 (see also FIGS. 13A, 13B and 14A to 14C).

Figure 6:
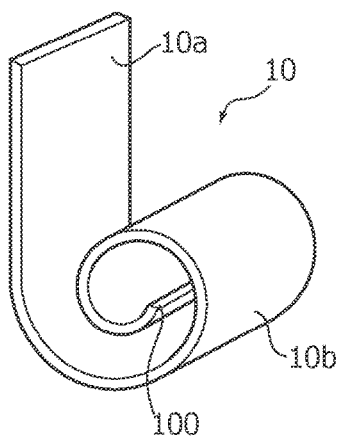
FIGS. 6 to 9 are exemplary of details of embodiments.
Figure 7:
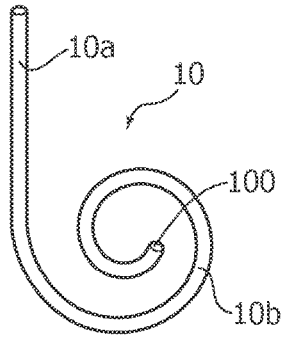
Figure 8:
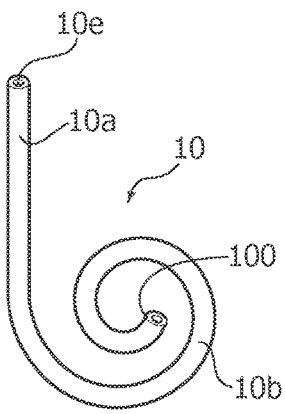

FIGS. 6 to 8 exemplify the possibility for the winding trajectory to the rolled up condition to include a spiral-like trajectory (i.e. lying in a single plane).

Figure 9:
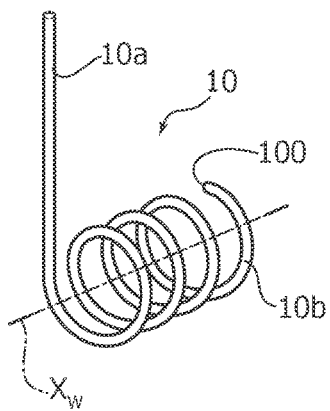

FIG. 9 exemplifies the possibility for the winding trajectory to the rolled up condition to include a helix-like trajectory (i.e. with the trajectory pitching into adjacent loops arranged side-by-side).

It will be appreciated that the winding trajectory being spiral-like or helix-shaped may be independent of the anchoring member 10 being blade-like or wire-like, solid or tubular.

Figure 10:
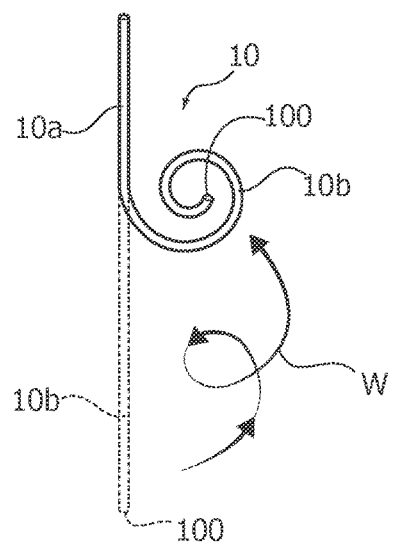
FIG. 10 and the sequence of FIGS. 11A to 11E are exemplary of possible kinematics of operation of embodiments.

FIG. 10 is exemplary of kinematics which may lead to the anchoring member 10 (e.g. the distal portion 10b in the exemplary embodiments considered herein) to wind or wrap from the deployed condition (shown in dashed lines) to the rolled up condition shown in full lines.

The arrow W is representative of the fact that such a winding or wrapping movement may involve a rotation in space of the distal end 100 of the anchoring member 10.

The related kinematics are further exemplified in FIGS. 11A to 11E.

Figure 11A:
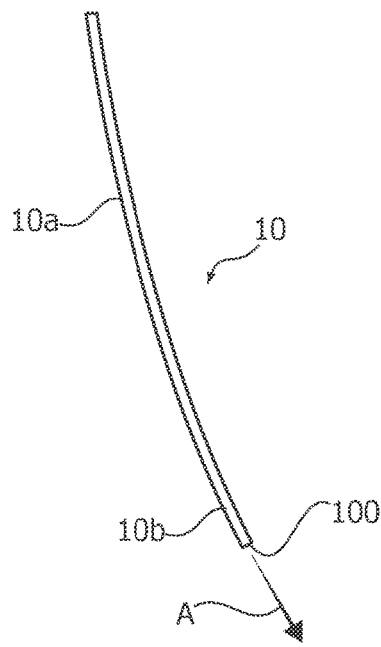

FIG. 11A is exemplary of an anchoring member 10 shown in the deployed condition. In one or more embodiments, the deployed condition of the anchoring member may not necessarily imply a rectilinear shape: as exemplified in FIG. 11A, the anchoring member 10 may be at least slightly arched in the deployed condition.

Figure 11B:
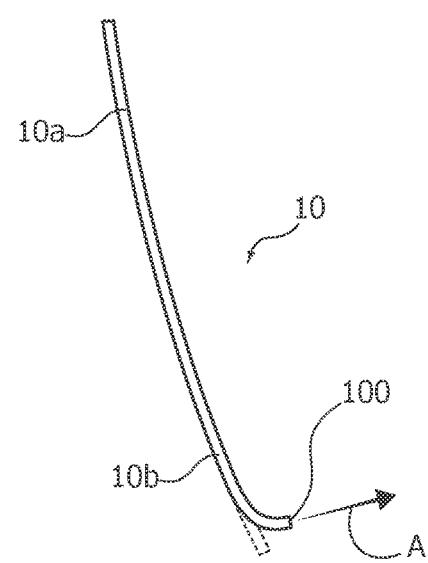
Figure 11C:
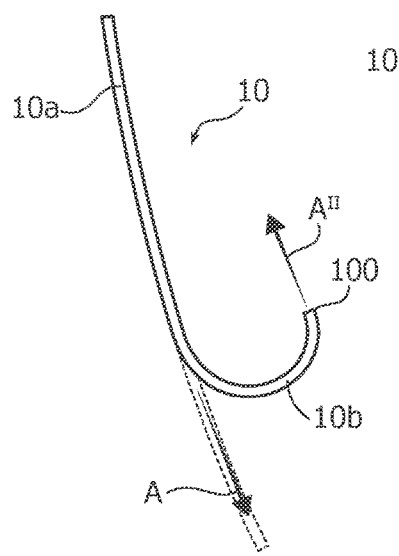
Figure 11D:
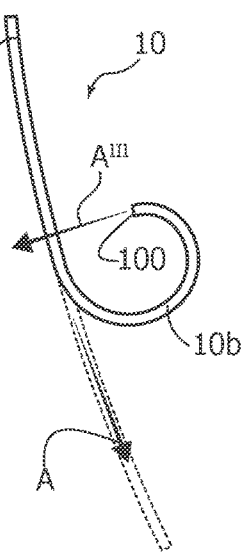
Figure 11E:
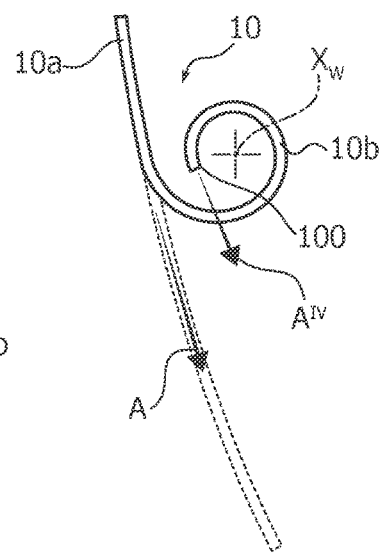

The sequence of FIGS. 11A to 11E is exemplary of a possible way of determining the angular extent of the winding or wrapping trajectory of the anchoring member 10 (e.g. due to elasticity and/or shape memory effect) from the deployed condition of FIG. 11A to the rolled up condition of FIG. 11E.

In the deployed condition of FIG. 11A, the distal portion 10b, and particularly the proximal end 100, points in a direction indicated by an arrow A.

FIGS. 11B, 11C and 11D are exemplary of intermediate stages of a winding/wrapping movement.

For instance, in winding from the deployed condition of FIG. 11A to the condition of FIG. 11B, the distal end 100 will undergo a rotation of 90° (that is with the distal end 100 pointing in direction $A^I$ at 90° to the pointing direction A of the deployed condition). Passing from the condition of FIG. 11A to the condition of FIG. 11B thus represent a winding trajectory having an angular extent of 90°.

In further winding from the condition of FIG. 11B to the condition of FIG. 11C, the distal end 100 will undergo a further rotation of 90° (that is with the distal end 100 pointing in direction $A^{II}$ at 180° to the pointing direction A of the deployed condition). Passing from the condition of FIG. 11A to the condition of FIG. 11C will thus represent a winding trajectory having an angular extent of 180°.

In further winding from the condition of FIG. 11C to the condition of FIG. 11D the distal end 100 will undergo a further rotation of 90° (that is with the distal end 100 pointing in direction $A^{III}$ at 270° to the pointing direction A of the deployed condition). Passing from the condition of FIG. 11A to the condition of FIG. 11D will thus represent a winding trajectory having an angular extent of 270°.

Finally, in further winding from the condition of FIG. 11D to the condition of FIG. 11E the distal end 100 will undergo a further rotation of 90° (that is with the distal end 100 pointing in direction $A^{IV}$ at 360° to the pointing direction A of the deployed condition). Passing from the condition of FIG. 11A to the condition of FIG. 11D thus represents a winding trajectory having an angular extent of 360°, that is a full loop or winding.

Reference $X_W$ in FIG. 11E denotes the center region (locus) of the—e.g. spiral-like—trajectory of the distal portion 10b the anchoring member 10 as finally rolled up (wound up) in the collapsed implantation condition. As indicated, in one or more embodiments the center region (e.g. axis) $X_W$ of the final collapsed trajectory of the anchoring member 10 may be at least approximately coplanar with the end plane OEP of the device V (see FIG. 3).

The examples of FIGS. 6 to 8 refer to possible embodiments (blade-like, wire-like or tubular, respectively) where winding/rolling to the final collapsed condition from a (notionally linear) deployed condition of the anchoring member 10 may involve a winding trajectory (that is a rotation of the distal end 100) having an angular extent in excess of 360° (e.g. 360°+90°=450° in the example of FIG. 8 and in excess of 450° in the examples of FIGS. 6 and 7).

The example of FIG. 9 refers to a possible embodiment wherein the helix-like winding trajectory to the rolled up condition from a notional linear deployed condition of the anchoring member 10 involves a winding trajectory (that is a rotation of the distal end 100) having an angular extent which may be a multiple of 360° (approximately 3×360°, namely 1080°) to a final winding center/axis $X_W$.

In one or more embodiments, the winding trajectory of the anchoring member 10 from the deployed condition to the rolled up condition may have an angular extent between 180° (half turn) and 900° (two turns and a half, i.e. 360°+360°+180°).

In one or more embodiments, the angular extent of the winding trajectory of the anchoring member 10 from the deployed condition to the rolled up condition may thus take into account factors such as the geometry of the body structure (e.g. valve annulus) used for anchoring and/or the nature of such a structure (e.g. soft/damaged tissue or leaflets).

In one or more embodiments, an implant device V may thus include anchoring members 10 having different angular extents of their winding trajectories in order to match different local characteristics of the anchoring body structure(s).

In one or more embodiments, the anchoring members (distal portion 10b subject to winding) may have a width between 0.2 mm and 5 mm: lower values may be optionally selected for wire-like members; higher values may be optionally selected for blade-like members.

In one or more embodiments, such widths may be constant.

In one or more embodiments, such widths may be vary over the length of the anchoring member e.g. to optimize the grasping action of the body tissues e.g. at the beginning and at the end of the rolling/winding action.

In one or more embodiments, the anchoring members (distal portion 10b subject to winding) may have a length between 1.5 mm and 25 mm.

In one or more embodiments, such values may be related to other parameters, e.g. a length of 1.5 mm being optionally selected for a winding trajectory over 180° to a final outer diameter of 1 mm and a length of 25 mm being optionally selected for a winding trajectory over 900° to a final outer diameter of 4 mm.

In one or more embodiments, the anchoring members (distal portion 10b subject to winding) may have a thickness between 0.1 and 0.5 mm.

In one or more embodiments, the final collapsed trajectory (e.g. spiral like) of the anchoring member—measured "in air", i.e. without any body structure grasped therein may involve a spacing (pitch) between adjacent turns or coils from zero (that is with no gaps or spacing therebetween) to 0.5 mm.

FIGS. 12A-12C, 13A-13B, 14A-14C, 15A-15B and 16A-16C are exemplary of various arrangements (or "kits") for implanting an implant device V according to one or more embodiments.

All these figures refer by way of the example to an implant device V such as e.g. a heart valve having a stent-like annular structure (armature) as exemplified in FIGS. 3 to 5, namely a tubular stent-like armature having a set of anchoring members 10 located at one end thereof (e.g. end plane OEP). As indicated, the embodiments are not limited to valve prostheses as the implant devices to be anchored to a patient body.

In one or more embodiments as exemplified herein, the proximal portions 10a of the anchoring members 10 are generally co-extensive with the stent-like structure of the valve prosthesis and, in the final rolled-up (collapsed) implant condition, the proximal portions 10b are intended to extend both radially and, at least partly, axially outwardly of the annular structure of the device V to provide anchoring of the implant device V to a body structure AS by protruding both radially and (at least in part) axially from one end (e.g. end plane OEP) of the annular structure.

Coupling of the anchoring members 10 to the implant device V may be e.g. according to any of the exemplary embodiments of FIGS. 3 to 5; any other type of feasible coupling may be included in one or more embodiments.

Figure 12A:
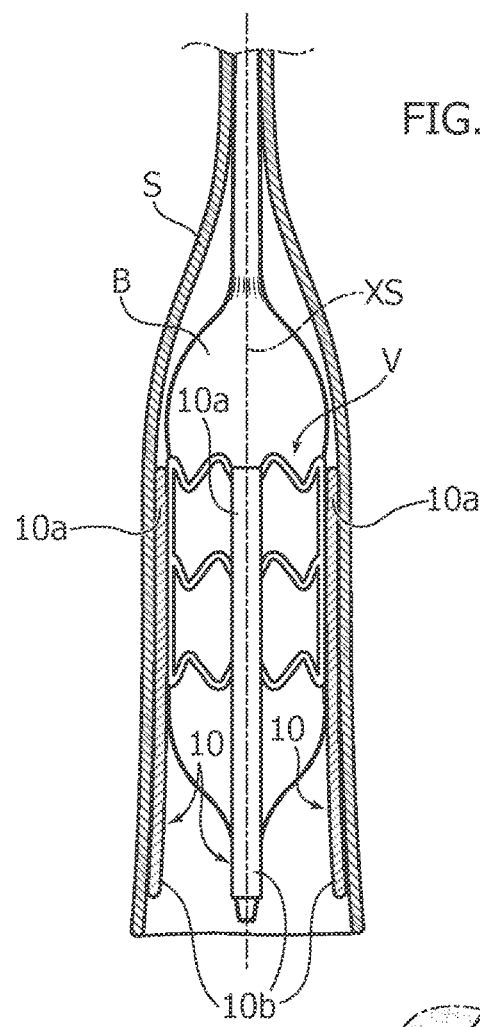
FIGS. 12A-12C are a first set of figures exemplary of implantation of embodiments.
Figure 12B:
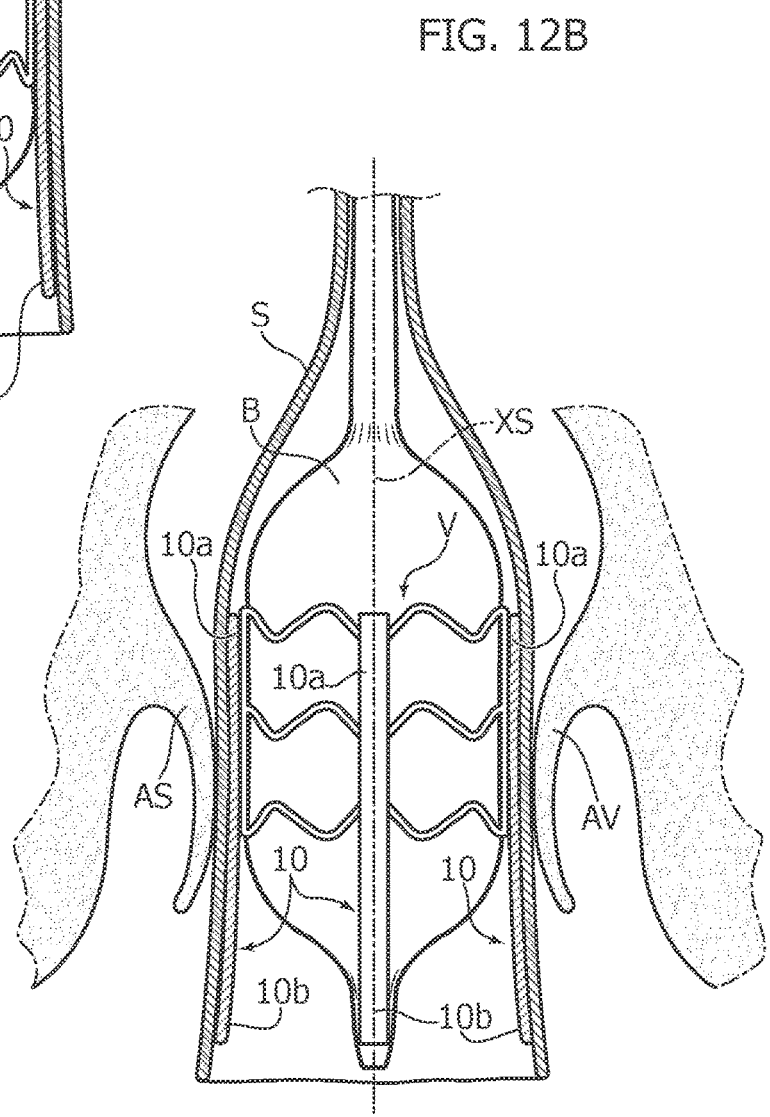
Figure 12C:
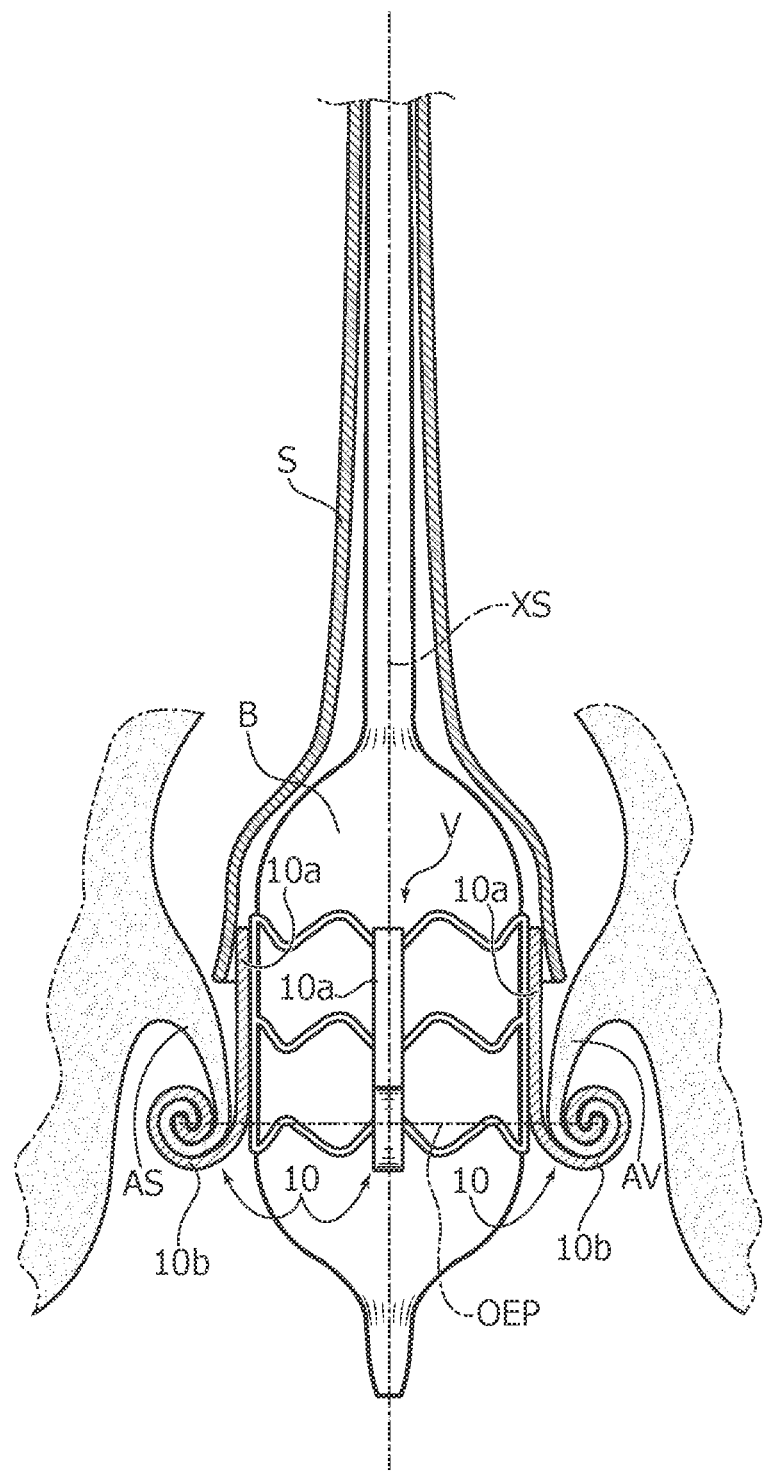

FIGS. 12B and 12C refer by way of example to implantation of a valve prosthesis V at an annular site. This may be e.g. a mitral site, that is between the left atrium and the left ventricle of the heart, in order to permit blood flow from the atrium into the ventricle (downwardly, with respect to the exemplary figures herein) while preventing blood flow in the opposite direction. By way of example, reference is made to implantation performed with the conservation of native valve structures such as the native leaflets AS (and the chordae tendinae, not visible in the figures).

One or more embodiments may lend themselves to such a technique, due to the capability of achieving secure anchoring of the valve V to the native valve structures without applying appreciable stress (particularly radial, i.e. dilation stress) onto these structures.

Figure 14B:
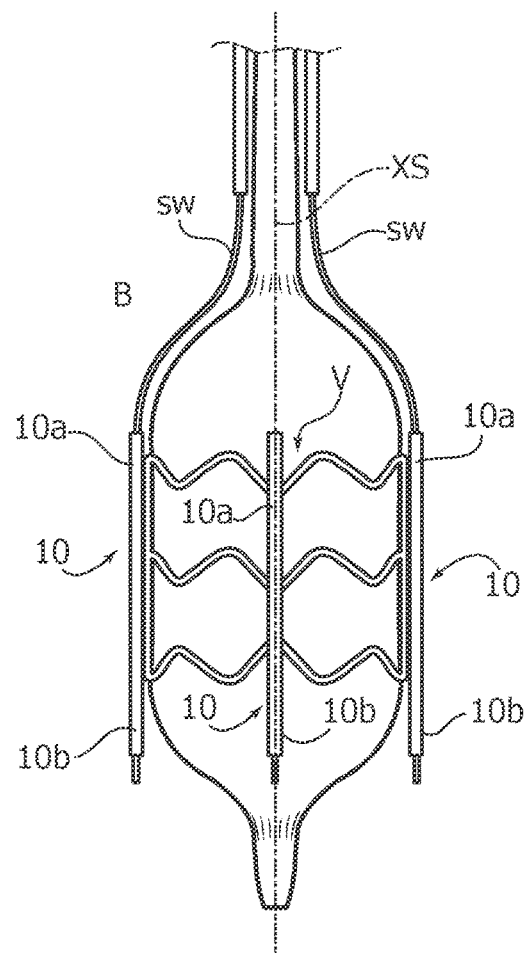
Figure 16A:
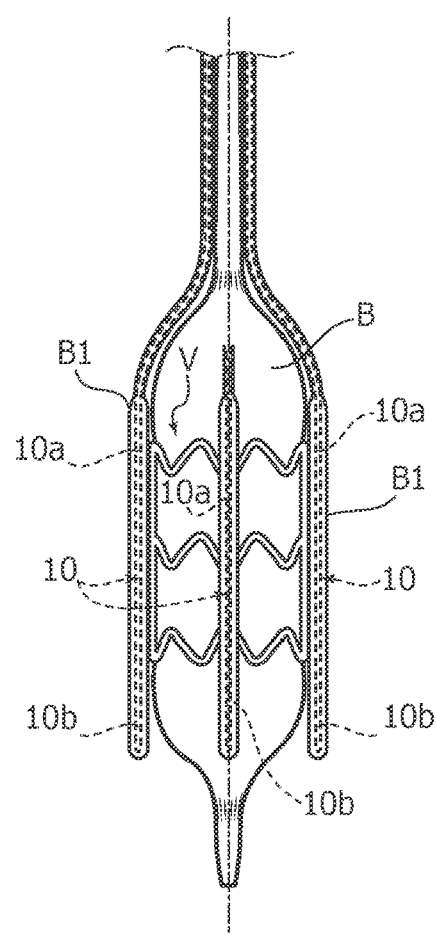

The various arrangements exemplified refer to an implant device (e.g. valve V) of a collapsible type, namely intended to be positioned at the implantation site in a radially contracted condition (see for instance FIGS. 12A, 14A and 16A) and then expanded to a radially expanded condition (see e.g. FIGS. 12B, 14B and 16B).

In one or more embodiments, as exemplified herein, radial expansion may be produced by means of a balloon catheter including a distal balloon B inflatable from a contracted condition (FIGS. 12A, 14A, 16A) to an inflated condition (FIGS. 12B-12C, 14B-14C and 16B-16C).

In one or more embodiments radial expansion of the implant device V may be by other means, e.g. due to self-expansion (elastic, shape memory) as known in the art.

The figures illustrate one or more embodiments of constraint members adapted to cooperate with the anchoring member(s) 10 in order to maintain the anchoring member(s) 10 in a deployed condition for insertion in the patient's body and positioning at the implantation site to then release the anchoring member(s) 10 to permit the winding/wrapping movement to a rolled up condition.

Such a winding/wrapping movement of the anchoring member(s) 10 (e.g. of the distal portions 10b, in the embodiments illustrated) may lead the or each member to grasp the anchoring body structure (for instance the native valve leaflets AS of FIGS. 12B and 12C) to secure anchoring of the implant device V at the implantation site, with minimum protrusion e.g. into the ventricular chamber.

In the arrangement of FIGS. 12A to 12C a constraint member may be in the form of a tubular sheath S extending along an axis XS, the sheath being arranged to surround the collapsed implant device V with the anchoring member or members 10 extended to the deployed condition (FIG. 12A). The sheath S may thus be able to maintain the anchoring member(s) 10 in the deployed condition by confining the anchoring member(s) by acting radially inwardly towards the axis XS.

As exemplified in FIG. 12B, the sheath S may be configured—for instance, by including an elastically deformable material such as e.g. silicone—in such way to allow the radial (e.g. as balloon-driven) expansion of the implant device V while still surrounding and thus constraining the anchoring member or members 10 to the deployed condition.

The sheath S may then withdraw along the axis XS as schematically represented in FIG. 12C in such a way as to uncover the anchoring member(s) 10 e.g. starting from the distal portion 10b. Being no longer constrained by the sheath S, the distal portion 10b will thus be able to undergo the winding/wrapping movement to the rolled up condition which provides anchoring to the body structures AS by having such structures wrapped by—and possibly within—the rolled up anchoring member(s) 10 (FIG. 12C).

A substantially similar delivery/implantation procedure may be adopted in the other exemplary arrangements illustrated in the subsequent figures, where various embodiments of constraint members are exemplified.

For instance, FIGS. 13A-13B refer to anchoring members 10 having a tubular structure and thus having a longitudinal cavity into which a stiffening wire or mandrel SW may be inserted to maintain (acting from inside) the anchoring member 10 in the deployed condition (e.g. a rectilinear or substantially rectilinear condition).

The stiffening wire SW may then withdrawn (i.e. extracted) out of the anchoring member 10 as schematically represented in FIG. 13B so that the anchoring member 10 (e.g. the distal portion 10b), being no longer stiffened by the wire SW inserted therein may undergo the winding/wrapping movement to the rolled up condition.

Figure 14C:
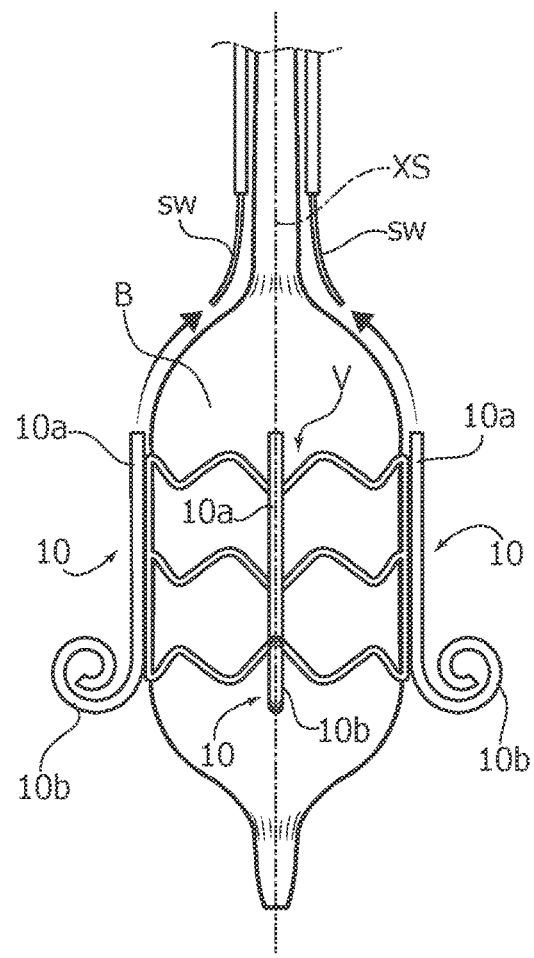

The sequence of FIGS. 14A to 14C exemplifies how an implantation procedure substantially corresponding to the one already exemplified in connection of FIGS. 12A to 12C may be performed by locating the implant device V at the implantation site in a radially contracted condition with the stiffening wire(s) SW inserted into the anchoring member(s) 10 to maintain it or them in the deployed condition as the implant device V is located at the implantation site and then expanded. The stiffening wire(s) SW may then be extracted from the anchoring member(s) 10 to permit winding/wrapping to the rolled up anchoring condition exemplified in FIG. 14C.

Figure 15A:
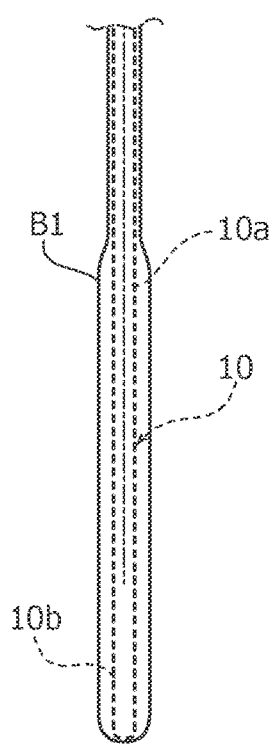
Figure 15B:
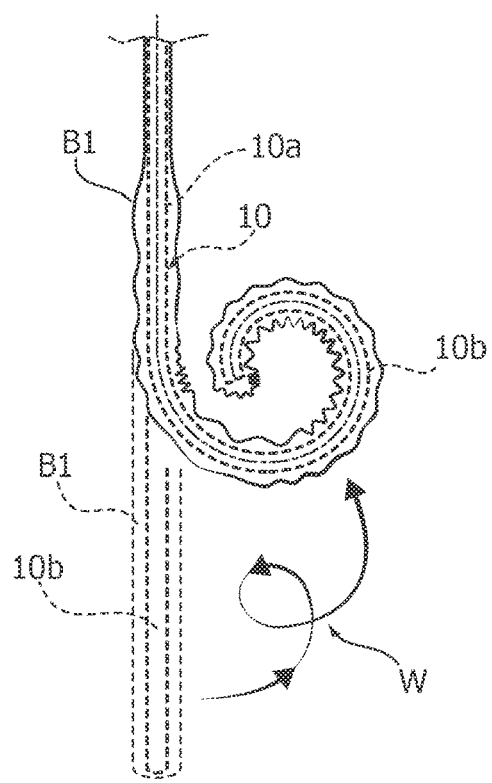

FIGS. 15A and 15B are exemplary of arrangements where a constraint action of the anchoring member(s) 10 to the deployed condition may be achieved by means of an inflatable balloon B1.

In one or more embodiments, such a balloon B1 may be a needle-like balloon as currently used to deliver and expand angioplasty stents such as e.g. coronary stents by means of balloon catheters.

In one or more embodiments, the balloon B1 may be of a "non-compliant" type.

In one or more embodiments, in the inflated condition as exemplified in FIG. 15A, the balloon B1 may constrain an anchoring member 10 inserted therein (that is with the balloon B1 vested onto the anchoring member 10 to form a tubular tunic around the member 10) with the capability of effectively resisting an elastic bias bestowed onto the anchoring member 10 to cause it to wind to the rolled up condition once no longer constrained.

The sequence of FIGS. 15A and 15B is exemplary of the balloon B1 being deflated (by known means). Once deflated, the balloon B1 becomes soft thus permitting the winding/wrapping movement of the anchoring member 10 located therein as exemplified in FIG. 15B.

The sequence of FIGS. 16A to 16C is exemplary of implantation procedures based on the same principles already described in connection with FIGS. 12A to 12C and 14A to 14C.

Specifically, FIG. 16A is exemplary of the implantation arrangement being in a radially contracted (collapsed) condition of the implant device V with the anchoring member(s) 10 maintained in the deployed condition by means of a stiffening balloon B1 in an inflated condition.

FIG. 16B is exemplary of radial expansion of the implant device V with the anchoring member(s) still maintained in the deployed condition by the balloon B.

Finally, FIG. 16C is exemplary of the balloon B1 being deflated so that the anchoring member(s), no longer retained to the extended condition, are permitted to wind/wrap to the rolled up anchoring condition of the implant device V.

The various exemplary implantation arrangements described herein lend themselves to be used both in connection with anchoring members that wind to the rolled up condition due to an elastic (e.g. super elastic) bias bestowed upon them and in connection with anchoring members that wind to the rolled up condition due to e.g. a shape memory effect other than elastic, such as a shape memory effect stimulated by the application of e.g. thermal, electrical or optical energy.

The details and embodiments may vary, even significantly, with respect to what has been described herein by way of the example only, without departing from the scope of protection. The extent of protection is determined by the claims that follow.

The invention claimed is:

1. An implant device for implantation in an animal body, the device including an annular structure extending axially between opposed ends and at least one elongated anchoring member deployable to a deployed condition for insertion into an animal body and retractable from said deployed condition to a rolled up condition wherein the anchoring member protrudes radially outwardly of the annular structure of the device to provide anchoring of the implant device to a body structure of an animal, wherein in said rolled up condition the anchoring member at least partly protrudes axially outwardly of the annular structure of the device, and wherein winding of the at least one elongated anchoring member from the deployed condition to the rolled up condition is with a winding trajectory having an angular extent between 180° and 900°.

2. The implant device of claim 1, wherein the at least one elongated anchoring member includes a proximal portion which retains the deployed condition and a distal portion subject to winding from the deployed condition to the rolled up condition.

3. The implant device of claim 1, wherein the anchoring member is located at one end of the annular structure of the device and includes a distal portion, which, in said rolled up condition, extends in a trajectory centered around a point coplanar with said one end of the annular structure of the device.

4. The implant device of claim 1, wherein the anchoring member includes a proximal portion coextensive with the annular structure of the device and a distal portion extending away from the annular structure of the device, wherein in said rolled up condition, the region of the said distal portion adjacent to said proximal portion has an axial orientation with respect to the annular structure of the device.

5. The implant device of claim 1, wherein the at least one elongated anchoring member includes elastic material, whereby the anchoring member is deployable to the deployed condition and elastically returns to the rolled up condition from the deployed condition.

6. The implant device of claim 1, wherein the at least one elongated anchoring member includes shape memory material, whereby the anchoring member returns to the rolled up condition from the deployed condition by shape memory effect.

7. The implant device of claim 1, wherein the at least one elongated anchoring member includes material selected out of one or combinations of flexibly resilient materials, medical grade materials, metal materials, plastics materials, shape memory materials, Nitinol, and stainless steel.

8. The implant device of claim 1, wherein winding of the at least one elongated anchoring member from the deployed condition to the rolled up condition is with a winding trajectory which is spiral-shaped or helix-shaped.

9. The implant device of claim 1, wherein winding of the at least one elongated anchoring member from the deployed condition to the rolled up condition is with a winding trajectory having an angular extent in excess of 360°.

10. The implant device of claim 1, wherein the at least one elongated member is blade-like or wire-like.

11. The implant device of claim 1, wherein the at least one elongated member is of solid cross-section or tubular.

12. The implant device of claim 1, wherein the device includes a prosthetic heart valve.

13. An implantation kit for an implant device including:
   an implant device according to claim 1,
   at least one constraint member to cooperate with the at least one anchoring member to constrain the at least one anchoring member to the deployed condition during insertion into an animal body and to permit winding of the at least one anchoring member to a rolled up condition to provide anchoring of the implant device to a body structure of an animal.

14. The kit of claim 13, wherein the at least one constraint member includes a tubular sheath extending along an axis, the tubular sheath maintaining the at least one anchoring member in the deployed condition by confining the at least one anchoring member radially of said axis, the tubular sheath withdrawable along said axis to at least partly uncover the at least one anchoring member to permit winding thereof to the rolled up condition.

15. The kit of claim 13, wherein the at least one anchoring member is tubular with a longitudinal cavity and the at least one constraint member includes a wire member for insertion into the longitudinal cavity of the at least one anchoring member to maintain the at least one anchoring member in the deployed condition, the wire member extractable from the longitudinal cavity of the at least one anchoring member to permit winding thereof to the rolled up condition.

16. The kit of claim 13, wherein the at least one constraint member includes an inflatable balloon element vested onto the at least one anchoring member to form a tubular tunic therearound, the inflated balloon to maintain the at least one anchoring member to the deployed condition and de-inflatable to permit winding of the at least one anchoring member to the rolled up condition.

17. An implant device for implantation in an animal body, the device including an annular structure extending axially between opposed ends and at least one elongated anchoring member deployable to a deployed condition for insertion into an animal body and retractable from said deployed condition to a rolled up condition wherein the anchoring member protrudes radially outwardly of the annular structure of the device to provide anchoring of the implant device to a body structure of an animal, wherein in said rolled up condition the anchoring member at least partly protrudes axially outwardly of the annular structure of the device, and wherein winding of the at least one elongated anchoring member from the deployed condition to the rolled up condition is with a winding trajectory having an angular extent in excess of 360°.

18. The implant device of claim 17, wherein the at least one elongated anchoring member includes a proximal portion which retains the deployed condition and a distal portion subject to winding from the deployed condition to the rolled up condition.

19. The implant device of claim 17, wherein winding of the at least one elongated anchoring member from the deployed condition to the rolled up condition is with a winding trajectory which is spiral-shaped or helix-shaped.

20. An implantation kit for an implant device including:
an implant device for implantation in an animal body, the device including an annular structure extending axially between opposed ends and at least one elongated anchoring member deployable to a deployed condition for insertion into an animal body and retractable from said deployed condition to a rolled up condition wherein the anchoring member protrudes radially outwardly of the annular structure of the device to provide anchoring of the implant device to a body structure of an animal, wherein in said rolled up condition the anchoring member at least partly protrudes axially outwardly of the annular structure of the device; and
at least one constraint member to cooperate with the at least one anchoring member to constrain the at least one anchoring member to the deployed condition during insertion into an animal body and to permit winding of the at least one anchoring member to a rolled up condition to provide anchoring of the implant device to a body structure of an animal,
wherein the at least one anchoring member is tubular with a longitudinal cavity and the at least one constraint member includes a wire member for insertion into the longitudinal cavity of the at least one anchoring member to maintain the at least one anchoring member in the deployed condition, the wire member extractable from the longitudinal cavity of the at least one anchoring member to permit winding thereof to the rolled up condition.

* * * * *